(12) United States Patent
Hebert et al.

(10) Patent No.: US 8,795,974 B2
(45) Date of Patent: Aug. 5, 2014

(54) ANTI-LG3 ANTIBODIES AND USES THEREOF

(75) Inventors: Marie-Josee Hebert, Outremont (CA); Heloise Cardinal, Montreal (CA); Nathalie Brassard, Montreal (CA)

(73) Assignee: Val-Chum, Limited Partnership, Montreal (CA)

( * ) Notice: Subject to any disclaimer, the term of this patent is extended or adjusted under 35 U.S.C. 154(b) by 0 days.

(21) Appl. No.: 13/583,414

(22) PCT Filed: Mar. 8, 2011

(86) PCT No.: PCT/CA2011/050133
§ 371 (c)(1),
(2), (4) Date: Sep. 7, 2012

(87) PCT Pub. No.: WO2011/109909
PCT Pub. Date: Sep. 15, 2011

(65) Prior Publication Data
US 2013/0004978 A1   Jan. 3, 2013

Related U.S. Application Data

(60) Provisional application No. 61/311,613, filed on Mar. 8, 2010.

(51) Int. Cl.
*G01N 33/53* (2006.01)
(52) U.S. Cl.
USPC .............................................. 435/7.1; 435/7.2
(58) Field of Classification Search
None
See application file for complete search history.

(56) References Cited

FOREIGN PATENT DOCUMENTS

WO    WO 2010015659    *  2/2010
WO    2011/050133       6/2011

OTHER PUBLICATIONS

Mayo Clinic Apr. 2014: Myocardial ischemia.*
Niiyama et al. J. Visualized Experiments Jan. 2009 p. 1-3.*
CA2011/050133 ISR, Jun. 17, 2011.
Cailhier, J.F., et al., Caspase-3 activation triggers extracellular cathepsin L release and endorepellin proteolysis. J Biol Chem, 2008. 283(40): p. 27220-9.
Cardinal, H., et al., Uraemic plasma decreases the expression of ABCA1, ABCG1 and cell-cycle genes in human coronary arterial endothelial cells. Nephrol Dial Transplant, 2007. 22(2): p. 409-16.
Colvin, R.B., Antibody-mediated renal allograft rejection: diagnosis and pathogenesis. J Am Soc Nephrol, 2007. 18(4): p. 1046-56.
Cornell, L.D., R.N. Smith, and R.B. Colvin, Kidney transplantation: mechanisms of rejection and acceptance. Annu Rev Pathol, 2008. 3: p. 189-220.
Couffinhal, T., et al., Mouse model of angiogenesis. Am J Pathol, 1998. 152(6): p. 1667-79.

Dragun, D., et al., Angiotensin II type 1-receptor activating antibodies in renal-allograft rejection. N Engl J Med, 2005. 352(6): p. 558-69.
Fukami, N., et al., Antibodies to MHC class I induce autoimmunity: role in the pathogenesis of chronic rejection. J Immunol, 2009. 182(1): p. 309-18.
Joosten, S.A. et al. "Antibody response against perlecan and collagen types IV and VI in chronic renal allograft rejection in the rat" Am. J. Pathol. (2002) 160(4): 1301-1310.
Joosten, S.A., et al., Antibody response against the glomerular basement membrane protein agrin in patients with transplant glomerulopathy. Am J Transplant, 2005. 5(2): p. 383-93.
Jurcevic, S., et al., Antivimentin antibodies are an independent predictor of transplant-associated coronary artery disease after cardiac transplantation. Transplantation, 2001. 71(7): p. 886-92.
Li, Y. et al., Insulin-like growth factor-1 receptor activation prevents high glucose-induced mitochondrial dysfunction, cytochrome-c release and apoptosis. Biochem Biophys Res Commun, 2009. 384(2): p. 259-64.
Oda, O., et al., Purification and characterization of perlecan fragment in urine of end-stage renal failure patients. Clin Chim Acta, 1996. 255(2): p. 119-32.
O'Riordan, E. et al. "Urinary proteomic analysis of chronic allograft nephropathy" Proteomics Clin. Appl. (2008) 2(7/8): 1025-1035.
Quintana, L.F. et al. "Urine proteomics biomarkers in renal transplantation: an overview" Transplantation (2009) 88(3S): S45-S49.
Racusen et al., Kidney International 55 (1999), pp. 713-723.
Raymond, M.A., et al., Apoptosis of endothelial cells triggers a caspase-dependent anti-apoptotic paracrine loop active on VSMC. FASEB J, 2004. 18(6): p. 705-07.
Reif, R. et al. "Specific cleavage of agrin by neurotrypsin, a synaptic protease linked to mental retardation" FASEB J. (2007) 21(13): 3468-3478.
Shimizu, A., et al., Kidney Int, 2000. 58: p. 2546-58.
Shimizu, A., et al., Lab Invest, 2002. 82(6): p. 673-86.
Shimizu, A., et al., Kidney Int, 2002. 61: p. 1867-1879.
Shimizu, A., et al., J Am Soc Nephrol, 2005. 16(9): p. 2732-45.
Solez, K., et al., Am J Transplant, 2008. 8(4): p. 753-60.
Soulez, M. et al. "Epidermal growth factor and perlecan fragments produced by apoptotic endothelial cells co-ordinately activate ERKI/2-dependent antiapoptotic pathways in mesenchymal stem cells" Stem Cells (2010) 28(4): 810-820.
Sumitran-Holgersson, S., et al., Identification of the nonclassical HLA molecules, mica, as targets for humoral immunity associated with irreversible rejection of kidney allografts. Transplantation, 2002. 74(2): p. 268-77.
Tyagi, N., et al., Mitochondrial mechanism of microvascular endothelial cells apoptosis in hyperhomocysteinemia. J Cell Biochem, 2006. 98(5): p. 1150-62.
Zhang, X. and E.F. Reed, Effect of antibodies on endothelium. Am J Transplant, 2009. 9(11): p. 2459-65.
Cai et al.—Incidence and role of antibody in graft injury: How can it best be monitored?, Transplantation Reviews, vol. 18, No. 4 (Oct. 2004): pp. 192-203.
PCT/CA2011050133 (year 2013), European Search Report issued in the corresponding European patent application.

* cited by examiner

*Primary Examiner* — Jacob Cheu
(74) *Attorney, Agent, or Firm* — Goudreau Gage Dubuc; Alain Dumont; S. Serge Shahinian

(57) ABSTRACT

A method for the prediction of the risk and/or the diagnosis of vascular damage such as acute vascular rejection in a subject, based on the determination of anti-LG3 antibodies levels in a sample from the subject, is disclosed.

19 Claims, 4 Drawing Sheets

```
   1 mgwraagall lalllhgrll avthglrayd glslpediet vtasqmrwth sylsddedml
  61 adsisgddlg sgdlgsgdfq mvyfralvnf trsieyspql edagsrefre vseavvdtle
 121 seylkipgdq vvsvvfikel dgwvfveldv gsegnadgaq iqemllrvis sgsvasyvts
 181 pqgfqfrrlg tvpqfpract eaefachsyn ecvaleyrcd rrpdcrdmsd elnceepvlg
 241 isptfsllve ttslpprpet timrqppvth apqpllpgsv rplpcgpqea acrnghcipr
 301 dylcdgqedc edgsdeldcg ppppcepnef pcgnghcalk lwrcdgdfdc edrtdeancp
 361 tkrpeevcgp tqfrcvstnm cipasfhcde esdcpdrsde fgcmppqvvt ppresiqasr
 421 gqtvtftcva igvptpiinw rlnwghipsh prvtvtsegg rgtliirdvk esdqgaytce
 481 amnargmvfg ipdgvlelvp qrgpcpdghf ylehsaaclp cfcfgitsvc qstrrfrdqi
 541 rlrfdqpddf kgvnvtmpaq pgtpplsstq lqidpslhef qlvdlsrrfl vhdsfwalpe
 601 qflgnkvdsy ggslrynvry elargmlepv qrpdvvlmga gyrllsrght ptqpgalnqr
 661 qvqfseehwv hesgrpvqra ellqvlqsle avliqtvynt kmasvglsdi amdttvthat
 721 shgrahsvee crcpigysgl scescdahft rvpggpylgt csgcncngha sscdpvyghc
 781 lncqhntegp qcnkckagff gdamkatats crpcpcpyid asrrfsdtcf ldtdgqatcd
 841 acapgytgrr cescapgyeg npiqpggkcr pvnqeivrcd ergsmgtsge acrcknnvvg
 901 rlcnecadgs fhlstrnpdg clkcfcmgvs rhctssswsr aqlhgaseep ghfsltnaas
 961 thttnegifs ptpgelgfss fhrllsgpyf wslpsrflgd kvtsyggelr ftvtqrsqpg
1021 stplhgqplv vlqgnniile hhvaqepspg qpstfivpfr eqawqrpdgq patrehllma
1081 lagidtllir asyaqqpaes rvsgismdva vpeetgqdpa leveqcscpp gyrgpscqdc
1141 dtgytrtpsg lylgtcercs chghseacep etgacqgcqh htegprceqc qpgyygdaqr
1201 gtpqdcqlcp cygdpaagqa ahtcfldtdg hptcdacspg hsgrhcerca pgyygnpsqg
1261 qpcqrdsqvp gpigcncdpq gsvssqcdaa gqcqckaqve gltcshcrph hfhlsasnpd
1321 gclpcfcmgi tqqcassayt rhlisthfap gdfqgfalvn pqrnsrltge ftvepvpega
1381 qlsfgnfaql ghesfywqlp etyqgdkvaa yggklrytls ytagpqgspl sdpdvqitgn
1441 nimlvasqpa lqgperrsye imfreefwrr pdgqpatreh llmaladlde lliratfssv
1501 plaasisavs levaqpgpsn rpraleveec rcppgyigls cqdcapgytr tgsglylghc
1561 elcecnghsd lchpetgacs qcqhnaagef celcapgyyg datagtpedc qpcacpltnp
1621 enmfsrtces lgaggyrcta cepgytgqyc eqcgpgyvgn psvqggqclp etnqaplvve
1681 vhparsivpq ggshslrcqv sgspphyfyw sredgrpvps gtqqrhqgse lhfpsvqpsd
1741 agvyictcrn lhqsntsrae llvteapskp itvteeqrs qsvrpgadvt fictaksksp
1801 aytlvwtrlh ngklptramd fngiltirnv qlsdagtyvc tgsnmfamdq gtatlhvqas
1861 gtlsapvvsi hppqltvqpg qlaefrcsat gsptptlewt ggpggqlpak aqihggilrl
1921 paveptdqaq ylcrahssag qqvaravlhv hggggprvqv spertqvhag rtvrlycraa
1981 gvpsatitwr keggslppqa rsertdiatl lipaittada gfylcvatsp agtaqariqv
2041 vvlsasdasp ppvkiesssp svtegqtldl ncvvagsaha qvtwyrrggs lpphtqvhgs
2101 rlrlpqvspa dsgeyvcrve ngsgpkeasi tvsvlhgths gpsytpvpgs trpiriepss
2161 shvaegqtld lncvvpgqah aqvtwhkrgg slparhqthg sllrlhqvtp adsgeyvchv
2221 vgtsgpleas vlvtieasvi pgpippvrie sssstvaegq tldlscvvag qahaqvtwyk
2281 rggslparhq vrgsrlyifq aspadagqyv crasngmeas itvtvtgtgq anlaypagst
2341 qpiriepsss qvaegqtldl ncvvpgqsha qvtwhkrggs lpvrhqthgs llrlyqaspa
2401 dsgeyvcrvl gssvpleasv lvtiepagsv palgvtptvr iessssqvae gqtldlnclv
2461 agqahaqvtw hkrggslpar hqvhgsrlrl lqvtpadsge yvcrvvgssg tqeasvlvti
2521 qqrlsgshsq gvaypvries ssaslanght ldlnclvasq aphtitwykr ggslpsrhqi
2581 vgsrlripqv tpadsgeyvc hvsngagsre tslivtiqgs gsshvpsvsp piriessspt
2641 vvegqtldln cvvarqpqai itwykrggsl psrhqthgsh lrlhqmsvad sgeyvcrann
2701 nidaleasiv isvspsagsp sapgssmpir iesssshvae getldlncvv pgqahaqvtw
2761 hkrggslpsh hqtrgsrlrl hhvspadsge yvcrvmgssg pleasvlvti easgssahv
2821 papggappir iepsssrvae gqtldlkcvv pgqahaqvtw hkrggnlpar hqvhgpllrl
2881 nqvspadsge yscqvtgssg tleasvlvti epsspgpipa pglaqpiyie assshvtegq
2941 tldlncvvpg qahaqvtwyk rggslparhq thgsqlrhl vspadsgeyv craasgpgpe
3001 qeasftvtvp psegssyrlr spvisidpps stvqqgqdas fkclihdgaa pislewktrn
3061 qeledvnhis pngsiitivg trpsnhgtyr cvasnaygva qsvvnlsvhg pptvsvlpeg
3121 pvwvkvgkav tlecvsagep rssarwtris stpakleqrt yglmdshavl qissakpsda
3181 gtyvclaqna lgtaqkqvev ivdtgamapg apqvqaeeae ltveaghtat lrcsatgspa
3241 ptihwsklrs plpwqhrleg dtliiprvaq qdsgqyicna tspaghaeat iilhvesppy
```

FIG. 3A

```
3301 attvpehasv qagetvqlqc lahgtppltf qwsrvgsslp gratarnell hferaapeds
3361 gryrcrvtnk vgsaeafaql lvqgppgslp atsipagstp tvqvtpqlet ksigasvefh
3421 cavpsdrgtq lrwfkeggql ppghsvqdgv lriqnldqsc qgtyicqahg pwgkaqasaq
3481 lviqalpsvl inirtsvqtv vvghavefec lalgdpkpqv twskvgghlr pgivqsggvv
3541 riahvelada gqyrctatna agttqshvll lvqalpqism pqevrvpags aavfpciasg
3601 yptpdiswsk ldgslppdsr lennmlmlps vrpqdagtyv ctatnrqgkv kafahlqvpe
3661 rvvpyftqtp ysflplptik dayrkfeiki tfrpdsadgm llyngqkrvp gsptnlanrq
3721 pdfisfglvg grpefrfdag sgmatirhpt plalghfhtv tllrsltqgs livgdlapvn
3781 gtsqgkfqgl dlneelylgg ypdygaipka glssgfigcv relriqgeei vfhdlnltah
3841 gishcptcrd rpcqnggqch dsesssyvcv cpagftgsrc ehsqalhchp eacgpdatcv
3901 nrpdgrgytc rchlgrsglr ceegvtvttp slsgagsyla lpaltnthhe lrldvefkpl
3961 apdgvllfsg gksgpvedfv slamvgghle fryelgsgla vlrsaeplal grwhrvsaer
4021 lnkdgslrvn ggrpvlrssp gksqglnlht llylggveps vplspatnms ahfrgcvgev
4081 svngkrldlt ysflgsqgig qcydsspcer qpcqhgatcm pageyefqcl crdgfkgdlc
4141 eheenpcqlr epclhggtcq gtrclclpgf sgprcqqgsg hgiaesdwhl egsggndapg
4201 qygayfhddg flafpghvfs rslpevpeti elevrtstas glllwqgvev geagqgkdfi
4261 slglqdghlv fryqlgsgea rlvsedpind gewhrvtalr egrrgsiqvd geelvsgrsp
4321 gpnvavnakg svyiggapdv atltggrfss gitgcvknlv lhsarpgapp pqpldlqhra
4381 qagantrpcp s
```

FIG. 3B

ANTI-LG3 ANTIBODIES AND USES THEREOF

CROSS-REFERENCE TO RELATED APPLICATIONS

This application is a National Entry Application of PCT application no PCT/CA2011/050133 filed on Mar. 8, 2011 and published in English under PCT Article 21(2), which itself claims the benefit of U.S Provisional Patent Application Ser. No. 61/311,613 filed on Mar. 8, 2010. All documents above are incorporated herein by reference in their entirety.

TECHNICAL FIELD

The present invention generally relates to vascular damage and transplant rejection, and more specifically to the diagnosis and prediction of vascular damage and/or acute vascular rejection and related diseases and conditions.

SEQUENCE LISTING

Pursuant to 37 C.F.R. 1.821(c), a sequence listing is submitted herewith as an ASCII compliant text file named "Sequence_listing", created on Mar. 8, 2011 and having a size of 39 kilobytes. The content of the aforementioned file is hereby incorporated by reference in its entirety.

BACKGROUND ART

Rejection of transplanted organs is the main barrier of transplantation today. It occurs as a result of humoral and cell-mediated responses by the recipient to specific antigens present in the donor tissue. These antigens are known as major histocompatibility complex (MHC) molecules. In humans, this group of molecules is referred to a human leukocyte antigen (HLA) complex molecules in humans.

Acute rejection usually occurs within the first weeks after transplantation. It is typically caused by mismatched HLA antigens that are present on all cells, which leads to activation of T cells in the host (or transplant recipient). HLA antigens are polymorphic therefore the chance of a perfect match is extremely rare. Endothelial cells in vascularized grafts such as kidneys are typically the earliest victims of acute rejection. Damage to the endothelial lining is often an early predictor of irreversible acute graft failure. The risk of acute rejection is highest in the first 3 months after transplantation, and is lowered by immunosuppressive agents in maintenance therapy.

The incidence of acute cellular rejection of renal allografts has decreased over the past decade (USRDS Annual Data Report, 2009). This has been attributed at least in part to the use of new immunosuppressive agents with higher potency on T-cell mediated responses. However, the incidence of acute rejection with evidence of vascular injury (i.e., transplant arteritis or capillaritis and/or C4d deposition) has not been positively impacted (USRDS Annual Data Report, 2009). In acute vascular rejection (AVR), cell-mediated, antibody-mediated and complement mediated pathways concur to vascular damage (Solez, K., et al., *Am J Transplant,* 2008. 8(4): p. 753-60). In most if not all forms of AVR of solid organ transplants, immune-mediated endothelial injury leading to a significant apoptotic response is a major characteristic (Solez, K., et al., supra; Shimizu, A., et al., *Kidney Int,* 2000. 58: p. 2546-58; Shimizu, A., et al., *Lab Invest,* 2002. 82(6): p. 673-86; Shimizu, A., et al., *Kidney Int,* 2002. 61: p. 1867-1879; Shimizu, A., et al., *J Am Soc Nephrol,* 2005. 16(9): p. 2732-45).

There is a need for the development of novel markers and methods for the prediction and/or diagnosis of acute vascular rejection, and/or for determining the risk of acute vascular rejection.

The present description refers to a number of documents, the content of which is herein incorporated by reference in their entirety.

SUMMARY OF THE INVENTION

In an aspect, the present invention provides a method for determining whether a subject is suffering from vascular damage, said method comprising:
(a) determining a level of antibodies directed against LG3 (anti-LG3) in a biological sample from said transplant recipient;
(b) comparing said level to a control level; and
(c) determining whether said subject is suffering from vascular damage based on said comparison.

In another aspect, the present invention provides a method for determining whether a candidate solid organ transplant recipient is at risk of suffering from acute vascular rejection (AVR), said method comprising:
(a) determining a level of antibodies directed against LG-3 (anti-LG3) in a biological sample from said candidate solid organ transplant recipient;
(b) comparing said level to a control level; and
(c) determining whether said candidate solid organ transplant recipient is at risk of suffering from AVR based on said comparison.

In another aspect, the present invention provides a method for monitoring the course of treatment of a subject suffering from vascular damage, the method comprising:
(a) determining a first level of antibodies directed against LG3 in a biological sample from subject;
wherein a decrease in said first level relative to a corresponding level determined in a corresponding biological sample obtained from said subject at an earlier time is indicative that said patient is responsive to said treatment, and wherein an absence of change or an increase in said first level relative to a corresponding level determined in a corresponding biological sample obtained from said subject at an earlier time is indicative that said patient is not responsive to said treatment.

In another aspect, the present invention provides a method to follow-up the condition of a solid organ transplant recipient, the method comprising:
(a) determining a first level of antibodies directed against LG-3 in a biological sample from said subject;
wherein a decrease in said first level relative to a corresponding level determined in a corresponding biological sample obtained from said solid organ transplant recipient at an earlier time is indicative that said solid organ transplant recipient condition has improved, and wherein an increase in said first level relative to a corresponding level determined in a corresponding biological sample obtained from said solid organ transplant recipient at an earlier time is indicative that said solid organ transplant recipient condition has deteriorated.

In another aspect, the present invention provides a kit or package comprising (i) means for determining the level of anti-LG3; and (ii) instructions setting forth the above-mentioned method.

In an embodiment, the above-mentioned subject is a solid organ transplant recipient and said vascular damage is acute vascular rejection (AVR).

In an embodiment, the above-mentioned solid organ transplant is renal transplant.

In an embodiment, the above-mentioned level of anti-LG3 is determined by an immunoassay.

In an embodiment, the above-mentioned determining comprises:

(i) contacting said biological sample with an LG3 polypeptide bound to a solid support to allow the formation of anti-LG3-LG3 polypeptide complex;

(ii) contacting said solid support with a second antibody recognizing said anti-LG3; and (iii) determining the level of said second antibody bound to said solid support.

In an embodiment, the above-mentioned second antibody is labeled or conjugated, in a further embodiment conjugated to an enzyme. In a further embodiment, the above-mentioned enzyme is horseradish peroxidase (HRP).

In an embodiment, the above-mentioned biological sample is a serum sample.

In an embodiment, the above-mentioned subject or candidate solid transplant recipient is human.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 3A and 3B show the amino acid sequence of human basement membrane-specific heparan sulfate proteoglycan core protein precursor (also known as perlecan, NCBI reference sequence No. NP_005520, SEQ ID NO:1), with the putative amino acids forming the LG3 domain depicted in bold.

DISCLOSURE OF INVENTION

Figure 1A:
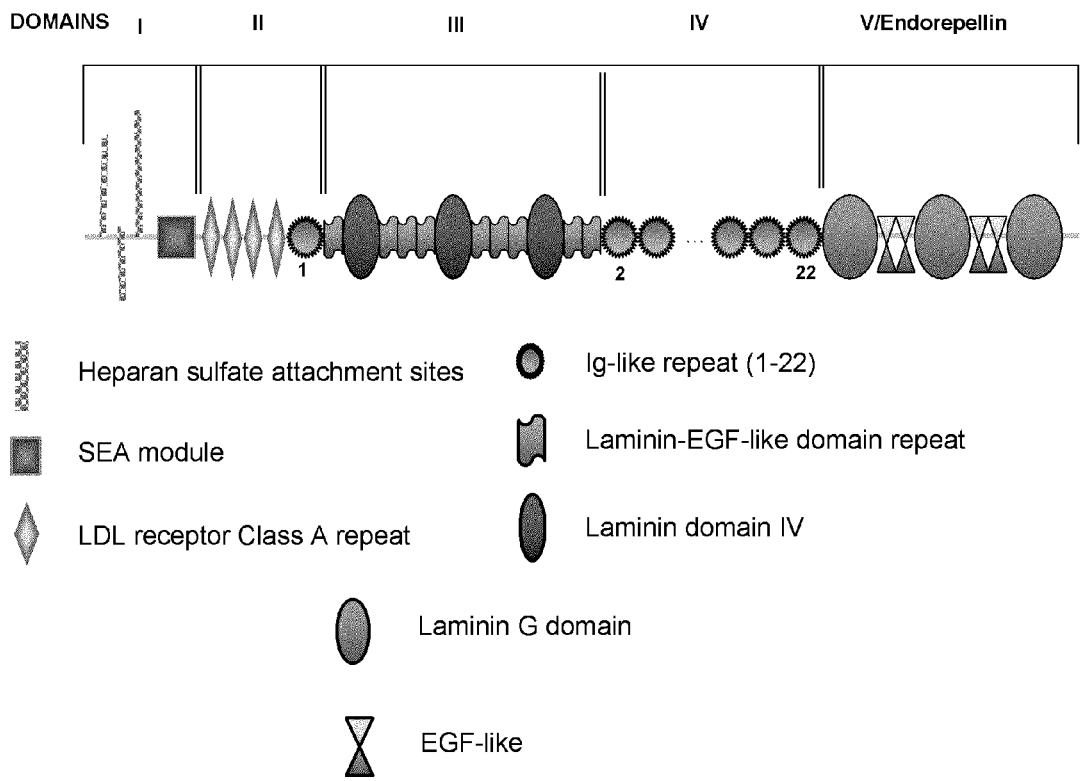
FIG. 1A shows the structure of perlecan.
Figure 1B:
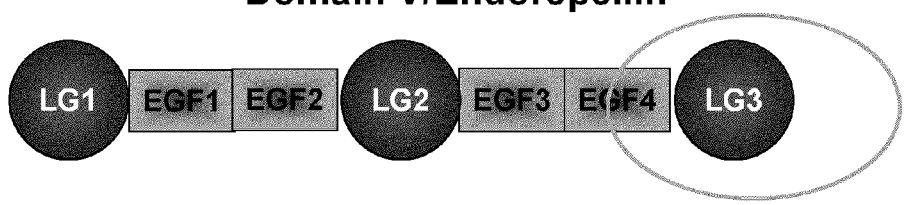
FIG. 1B shows the structure of Domain V/Endorepellin of perlecan, with the C-terminal LG3 domain circled.

In the studies described herein, the present inventors have demonstrated that increased/elevated levels of antibodies directed against LG3, a C-terminal fragment of the domain V of the heparan sulfate proteoglycan perlecan polypeptide (FIG. 1), are associated with acute vascular rejection. More specifically, it was shown that subjects having elevated anti-LG3 levels before and after solid transplantation are more likely to experience acute vascular rejection following transplantation, relative to subjects having lower anti-LG3 levels. The present inventors have also demonstrated that the level of anti-LG3 antibodies increases following ischemia induced by femoral artery ligation in mice Accordingly, in a first aspect, the present invention provides a method for determining whether a candidate solid transplant recipient is at risk of suffering from acute vascular rejection, said method comprising:

(a) determining a level of antibodies directed against LG-3 (anti-LG3) in a biological sample from said candidate solid transplant recipient;

(b) comparing said level to a control level; and (c) determining whether said subject is at risk of suffering from AVR based on said comparison.

In another aspect, the present invention provides a method for determining whether a subject (e.g., a solid transplant recipient) is suffering from vascular damage (e.g., acute vascular rejection), said method comprising:

(a) determining a level of antibodies directed against LG3 (anti-LG3) in a biological sample from said subject;

(b) comparing said level to a control level; and (c) determining whether said subject is suffering from vascular damage based on said comparison.

The values for anti-LG3 levels can be absolute or relative values, e.g., values provided in comparison to control levels. The values for expression levels can be raw values, or values that are optionally rescaled, filtered and/or normalized. The approach used will depend, for example, on the intended use for the data. The values for anti-LG3 levels may correspond to the intensity of a signal measured using a suitable device (e.g., optical density (OD) values at a given wavelength measured using a spectrometer), or to an estimated anti-LG3 levels (based on a standard curve established using known concentrations of anti-LG3, for example).

"Control level" or "reference level" or "standard level" are used interchangeably herein and broadly refers to a separate baseline level measured in a comparable control sample, which is generally from a subject not suffering from vascular damage or acute vascular rejection or not at risk of suffering from acute vascular rejection. The corresponding control level may be a level corresponding to an average or median level calculated based of the levels measured in several reference or control subjects (e.g., a pre-determined or established standard level). The control level may be a pre-determined "cut-off" value recognized in the art or established based on levels measured in one or a group of control subjects. The corresponding reference/control level may be adjusted or normalized for age, gender, race, or other parameters. The "control level" can thus be a single number/value, equally applicable to every patient individually, or the control level can vary, according to specific subpopulations of patients. Thus, for example, older men might have a different control level than younger men, and women might have a different control level than men. The predetermined standard level can be arranged, for example, where a tested population is divided equally (or unequally) into groups, such as a low-risk group, a medium-risk group and a high-risk group or into quadrants or quintiles, the lowest quadrant or quintile being individuals with the lowest risk (i.e., lowest amount of anti-LG3) and the highest quadrant or quintile being individuals with the highest risk (i.e., highest amount of anti-LG3).

It will also be understood that the control levels according to the invention may be, in addition to predetermined levels or standards, anti-LG3 levels measured in other samples (e.g. from healthy/normal subjects) tested in parallel with the experimental sample.

In an embodiment, the control level is a corresponding level or standard established based on anti-LG3 levels in subjects not suffering from vascular damage or AVR, or not at risk of suffering from AVR. In such a case, higher anti-LG3 levels measured in a sample from subject relative to the control level is indicative that the subject is suffering from vascular damage or acute vascular rejection, or is at risk (or is at high risk) of suffering from acute vascular rejection (i.e. less likely to be a patient with normal graft function), whereas similar or lower anti-LG3 levels measured in a sample from subject relative to the control level is indicative that the subject is not suffering from vascular damage or acute vascular rejection, or is not at risk (or is at low risk) of suffering from acute vascular rejection (i.e., more likely to be a patient with normal graft function).

In another embodiment, the control level is a corresponding level or standard established based on anti-LG3 levels in subjects known to suffer from vascular damage or AVR, or known to be at risk of suffering from AVR. In such a case, similar or higher anti-LG3 levels measured in a sample from the subject relative to the control level is indicative that the subject is suffering from vascular damage or AVR, or is at risk (or at high risk) of suffering from acute vascular rejection (i.e. less likely to be a patient with normal graft function), whereas lower anti-LG3 levels measured in a sample from subject relative to the control level is indicative that the subject is not suffering from vascular damage or AVR, or is not at risk (or is at low risk) of suffering from acute vascular rejection (i.e., more likely to be a patient with normal graft function).

In an embodiment, the above-mentioned biological sample is a biological fluid, e.g., urine, saliva, lymph, or a blood-derived sample. The term "blood-derived sample" as used herein refers to blood (e.g., fresh blood, stored blood) or to a fraction thereof, such as serum, plasma and the like. It also refers to any sample that may be obtained following one or more purification, enrichment, and/or treatment steps using blood (obtained by venous puncture, for example) as starting material. In an embodiment, the above-mentioned blood-derived sample is serum.

In another aspect, the present invention provides a method for monitoring the course of treatment of a subject (e.g., a transplant recipient) suffering from vascular damage or acute vascular rejection, the method comprising: (a) determining a first level of antibodies directed against LG3 in a biological sample from said subject; wherein a decrease in said level relative to a corresponding level determined in a corresponding biological sample obtained from said subject at an earlier time is indicative that said patient is responsive to said treatment, and wherein an absence of change or an increase in said first level relative to a corresponding level determined in a corresponding biological sample obtained from said subject at an earlier time is indicative that said patient is not responsive to said treatment.

In another aspect, the present invention provides a method to follow-up the condition of a subject suffering from vascular damage (e.g., a subject who underwent solid organ transplantation), the method comprising:

(a) determining a first level of antibodies directed against LG3 in a biological sample from said subject; wherein a decrease in said first level relative to a corresponding level determined in a corresponding biological sample obtained from said subject at an earlier time (e.g., at an earlier time point but after transplantation) is indicative that said patient condition has improved (e.g., that the patient is less likely to develop acute vascular rejection than before, or that the acute vascular rejection is less severe relative to the earlier time point), and wherein an increase in said first level relative to a corresponding level determined in a corresponding biological sample obtained from said subject at an earlier time (e.g., at an earlier time point but after transplantation) is indicative that said patient condition has deteriorated (e.g., that the patient is more likely to develop acute vascular rejection than before, or that the acute vascular rejection is more severe relative to the earlier time point). Such method permits to determine for example whether the extent or severity of the vascular damage or AVR is worsening or improving.

The invention further provides methods for developing personalized treatment plans. Information gained by way of the methods described above can be used to develop a personalized treatment plan for subjects suffering from vascular damage (e.g., acute transplant rejection), or deemed at risk of suffering from acute transplant rejection. Accordingly, the invention further provides methods for developing personalized treatment plans for subjects suffering from vascular damage (e.g., acute transplant rejection), such as solid organ transplant recipients (e.g., renal or kidney transplant recipients). The methods can be carried out by, for example, using the methods described above and, in consideration of the results obtained, designing a treatment plan for the subject. If the level of anti-LG3 indicates that the subject is suffering from, or at risk of suffering from, vascular damage (e.g., acute transplant rejection), the subject is a candidate for treatment with an effective amount of a drug for treating the condition (e.g., an anti-rejection agent). Depending on the amount of anti-LG3 detected, the subject may require a treatment regime that is more aggressive (e.g., if the anti-LG3 level is very high as compared to a normal control level) than a standard regime, or it may be determined that the subject is best suited for a standard regime. When so treated, one can treat or prevent complications associated with the condition. Conversely, a different result (i.e., a normal anti -LG3 level) may indicate that the subject is not experiencing (or is not likely to experience) an undesirable clinical outcome. In that event, the patient may avoid a treatment regime (or require a less aggressive regime) and their associated side effects.

The therapy (e.g., anti-rejection therapy), if deemed advisable, can be carried out with any of the presently used therapeutic agents for the condition to be treated. Generally, these agents are suspended in carriers/excipients (physiological saline) and administered orally or by inhalation or intravenous infusion, or injected or implanted in a variety of ways. The standard dosage may be increased or decreased, depending on the results of the anti-LG3 level analysis. For example, dosage may be at least 2-fold, 3-fold, 4-fold, 6-fold, 8-fold, 10-fold, 20-fold, 50-fold, 100-fold, or 150-fold more or less than the dosage the patient would ordinarily receive.

Methods to measure the amount/level of antibodies (e.g., anti-LG3) are well known in the art. Antibody levels may be detected either directly using affinity reagents, such as an antibody or a fragment thereof (for methods, see for example Harlow, E. and Lane, D (1988) Antibodies: A Laboratory Manual, Cold Spring Harbor Laboratory Press, Cold Spring Harbor, N.Y.), or a first ligand (natural or synthetic) which binds the anti-LG3 antibody (e.g., an LG3 polypeptide/protein or a fragment thereof). Such first ligand may be labeled/conjugated, e.g., radio-labeled, chromophore-labeled, fluorophore-labeled, or enzyme-labeled to facilitate detection and quantification of the complex (direct detection). Alternatively, the anti-LG3/ligand complex may be detected using a second ligand specifically recognizing the first ligand (indirect detection). Such second ligand may be radio-labeled, chromophore-labeled, fluorophore-labeled, or enzyme-labeled to facilitate detection and quantification of the complex. Enzymes used for labelling antibodies for immunoassays are known in the art, and the most widely used are horseradish peroxidise (HRP) and alkaline phosphatase (AP).

LG3 polypeptide/protein as used herein refers to a C-terminal domain of the perlecan polypeptide (FIGS. 1B and 3A-3B, SEQ ID NO:1), in an embodiment a domain comprising an amino acid sequence corresponding to about residues 4197 to about residue 4391 of the amino acid sequence of FIGS. 3A and 3B (SEQ ID NO:1), in a further embodiment form about residue 4203 to about residue 4362 of the amino acid sequence of FIGS. 3A and 3B (SEQ ID NO:1). In an embodiment, the above-mentioned LG3 polypeptide/protein is a human LG3 polypeptide/protein. LG3 polypeptide/protein fragment refers to a portion of the LG3 polypeptide/protein defined above and that is capable of binding to anti-LG3 antibodies present in biological samples from subjects, e.g., a portion of the LG3 polypeptide/protein preferentially targeted by the anti-LG3 antibodies.

Examples of methods to measure the amount/level of anti-LG3 antibodies include, but are not limited to: Western blot, immunoblot, enzyme-linked immunosorbant assay (ELISA), radioimmunoassay (RIA), immunoprecipitation, surface plasmon resonance (SPR), chemiluminescence, fluorescent polarization, phosphorescence, immunohistochemical analysis, matrix-assisted laser desorption/ionization time-of-flight (MALDI-TOF) mass spectrometry, microcytometry, microarray, antibody array, microscopy, flow cytometry, proteomic-based assays, and assays based on a property of the antibody including but not limited to ligand binding or interaction with other protein partners.

In an embodiment, the level of anti-LG3 antibody within the methods of the present invention is determined using by an immunoassay (e.g., ELISA), for example using a native or recombinant LG3 polypeptide/protein (or a fragment thereof capable of binding to anti-LG3 antibodies present in a biological sample) and anti-IgG antibodies. In an embodiment, the recombinant LG3 polypeptide/protein (or a fragment thereof) is immobilized on a solid support, such as magnetic or chromatographic matrix particles, the surface of an assay plate (such as microtiter wells), pieces of a solid substrate material (such as plastic, nylon, paper), and the like. The biological sample (e.g., serum) of the subject is then put in contact with the solid support coated with the LG3 polypeptide/protein so that the anti-LG3 antibodies present in the sample binds to the attached LG3 polypeptide/protein. The solid support may be washed one or more times, and a ligand (which is preferably labelled to facilitate detection) recognizing the anti-LG3 antibodies (e.g., an anti-Ig antibody or a fragment thereof) is put in contact with the coated solid support to measure the amount of anti-LG3 bound to the plate (which is representative of the level of anti-LG3 antibody present in the sample). The amount of ligand recognizing the anti-LG3 antibodies (e.g., an anti-Ig antibody or a fragment thereof) is determined using any methods known in the art, for example radiometric-, colorimetric-, fluorometric- or enzymatic-based methods. Thus, the solid support will contain labels in proportion to the amount of secondary antibody bound to the plate. If the label is an enzyme (e.g., HRP, AP), a substrate for the enzyme may be applied, and catalysis by the enzyme leads to a measurable signal, for example a change in color or fluorescence, which may be measured using a spectrometer, for example (or any other device capable of detecting changes in color or fluorescence). The intensity of the signal is indicative of or proportional to the amount of the anti-LG3 in the sample, and may be compared to a control. The intensity of the signal may be transformed into a corresponding anti-LG3 level using a known standard (i.e. based on the signal obtained with a sample that contains a known concentration of anti-LG3 antibodies, or a plurality of such samples to establish a standard curve). In an embodiment, the above-mentioned anti-LG3 levels are determined based on the optical density The term "antibody" as used herein encompasses monoclonal antibodies, polyclonal antibodies, multispecific antibodies (e.g., bispecific antibodies), and antibody fragments, so long as they exhibit the desired biological activity or specificity (i.e. binding to LG3 and/or to a fragment thereof). "Antibody fragments" comprise a portion of a full-length antibody, generally the antigen binding or variable region thereof. Interactions between antibodies and a target polypeptide are detected by radiometric, colorimetric, or fluorometric means. Detection of antigen-antibody complexes may be accomplished by addition of a secondary antibody that is coupled/conjugated to a detectable tag, such as an enzyme, fluorophore, or chromophore.

The analysis of anti-LG3 levels could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" (see, e.g., Ng and Ilag, *J. Cell Mol. Med.* 6: 329-340, 2002) and capillary devices.

In an embodiment, the above-mentioned methods are performed in vivo or in vitro, in a further embodiment in vitro.

The present invention also provides a kit or package comprising means/reagents useful for determining the amount/level of anti-LG3, for example one or more ligands that specifically bind to anti-LG3 antibodies, such as a specific antibody and/or LG3 polypeptide (or fragments thereof). Such kit may further comprise, for example, instructions setting forth the above-mentioned methods (i.e., instructions for predicting the risk and/or diagnosing vascular damage/acute vascular rejection, for following-up the course of treatment or condition of a subject), control samples (e.g., samples to which the test sample may be compared to establish the diagnostic/prediction), containers, reagents useful for performing the methods (e.g., buffers, enzymes, containers, immunodetection reagents, etc). The kit may further include where necessary agents for reducing background interference in a test, agents for increasing signal, software and algorithms for combining and interpolating values to produce a prediction of clinical outcome of interest, apparatus for conducting a test, calibration curves and charts, standardization curves and charts, and the like.

As used herein the term "subject" is meant to refer to any animal, such as a mammal including human, mice, rat, dog, cat, pig, cow, monkey, horse, etc. In an embodiment, the above-mentioned subject is a mammal, in a further embodiment a human. In an embodiment, the above-mentioned subject is a transplant recipient (or a candidate transplant recipient), such as a bone marrow or solid organ transplant recipient. In a further embodiment, the above-mentioned subject is a solid organ transplant recipient, such as a kidney/renal transplant recipient, a heart transplant recipient, a lung transplant recipient, or a pancreas transplant recipient. In an embodiment, the subject suffers from acute vascular rejection or is at risk of (i.e., has a predisposition for) suffering from acute/active vascular rejection. In an embodiment, the above-mentioned subject suffers from acute tubulo-interstitial rejection (ATIR). In an embodiment, the above-mentioned acute vascular rejection is a Banff 97 classification grade IIa, IIb and/or III acute vascular rejection or an acute, antibody-mediated rejection. The Banff 97 classification is an internationally recognized classification system for the diagnosis of renal allograft pathology (Racusen et al., Kidney International 55 (1999), pp. 713-723). Grade IIa typically defines cases with mild to moderate intimal arteritis (v1); grade IIb typically defines cases with several intimal arteritis comprising >25% of the luminal area (v2); and grade III typically defines cases with transmural arteritis and/or arterial fibrinoid change and necrosis of medial smooth muscle cells (v3 with accompanying lymphoctic inflammation). Antibody-mediated rejection is characterized by positive C4d staining in the graft peritubular capillaries, in the presence of anti-donor specific antibody (anti-HLA) in the circulation, a histologic appearance of acute tubular necrosis, peritubular capillaritis, glomerulitis or endarteritis.

In another embodiment, the above-mentioned subject suffers from vascular damage associated with ischemia (ischemic vascular damage) or other conditions, such as peripheral atherosclerotic vascular disease, post-myocardial infarction or post-acute kidney injury.

MODE(S) FOR CARRYING OUT THE INVENTION

The present invention is illustrated in further details by the following non-limiting examples.

EXAMPLE 1

Materials and Methods

Design. A retrospective case-control study was performed in which 2 groups of patients were selected according to the post-transplant occurrence of the following conditions: acute vascular rejection (AVR) or normal function of the renal allograft. Circulating levels of anti-LG3 antibodies were measured before transplantation and as close as possible to the time of rejection in the AVR group.

Patients. Clinical information on the post-transplant evolution of all kidney transplant recipients at the Centre Hospitalier de l'Université de Montréal is prospectively entered in a computerized database. All subjects who received a kidney transplant between Jan. 1, 1990 and Jan. 7, 2009 were screened for inclusion in this study with the use of this electronic database. All biopsies were performed for cause. All patients with AVR, defined as Banff 1997 class II or III cell-mediated rejection or antibody-mediated rejection, were included in this study. Normal controls were chosen from the same period of transplantation (±2 years) and had a normally functioning renal allograft.

Measurements. As of January 1985, sera from all consecutive patients receiving a kidney transplantation at the Centre Hospitalier de l'Université de Montréal were collected and stored (−80° C.) at different time points (pre-transplantation, and weekly for the first 4 weeks after transplantation). The primary outcomes were the presence of anti-LG3 antibodies in subjects with AVR compared to normal controls. They were measured immediately prior to transplantation and at one time point after transplantation. In subjects with AVR, we measured the post-transplant anti-LG3 antibodies on the serum that was collected closest to the date of diagnosis, and always within 3 weeks preceding it. Levels of anti-LG3 antibodies were measured by a locally developed ELISA. The recombinant LG3 protein was first coated onto a Immulon-IIHB™ plate (96 wells), using a 10 ng/µl concentration, for a total of 1000 ng per well. Sera were diluted (1/250) and deposited on the plaque. After washing, an anti-human IgG antibody coupled with horseradish peroxidase (HRP, Amersham) was incubated with sera. The colorimetric reaction was revealed with TMB substrate (BD Biosciences) on the plaque. Spectrophotometric analysis was performed at 450 nm.

Statistical analysis. Normally distributed continuous variables are presented as mean and standard deviation (SD), and non-normally distributed variables, as median with interquartile range ($25^{th}$ and $75^{th}$ percentile). Categorical variables are summarized using proportions. A Wilcoxon rank sum test was used to compare anti-LG3 levels before and after transplantation in subjects with AVR and those with a normally functioning graft.

EXAMPLE 2

Anti-LG3 Levels Pre- and Post-Transplantation

Anti-LG3 serum levels were measured before transplantation in 23 renal transplant patients with AVR and 45 renal transplant patients with normal renal allograft function. Post-transplantation sera were available in 20 subjects with AVR and 39 subjects with a normal graft. In the AVR group, 19 patients were de novo renal transplant patients and 4 subjects had received an organ transplant in the past. In patients with normal allograft function, 44 patients were de novo renal transplant patients and 1 patient had received a renal allograft in the past. One AVR case occurred 6 months after transplantation, and anti-LG3 levels were measured on the day of the biopsy in this patient. For all other subjects, post-transplant anti-LG3 levels were assessed within 2 months after transplantation. In both groups the median time elapsed between transplantation and blood sampling was 2 weeks. At the time of post-transplant blood sampling, 50% of AVR patients required dialysis support and the median blood creatinine level was 145 µmol/l in AVR patients who did not require renal replacement therapy. In the normal group, the median blood creatinine level was 108 µmol/l.

As shown in Table I, there was a clear trend for higher pre-transplant anti-LG3 levels in patients with AVR as compared to normal transplant controls (Wilcoxon rank sum test (2 tailed): p=0.09). Anti-LG3 levels higher than 616 (OD at 450 nm) were found exclusively in patients with AVR.

TABLE I

| ELISA anti-LG3 PRE-Transplantation | | | |
|---|---|---|---|
| | Median OD | (Interquartile range) | (range) |
| Acute vascular rejection (n = 23): | 183 | (90-269) | (50-960) |
| Normal renal allograft (n = 23): | 99 | (74-196) | (6-616) |

The results above show that high titers of anti-LG3 antibodies before transplantation are associated with AVR. High anti-LG3 titers (OD at 450 nm above 200) were found in de novo renal transplant patients.

As shown in Table II, post-transplant anti-LG3 levels tended to be lower in AVR patients, compared with pre-transplant levels. However, post-transplant anti-LG3 levels were significantly higher in patients with AVR compared with normal transplant controls (Wilcoxon rank sum test (2 tailed): p=0.02).

TABLE II

| ELISA anti-LG3 POST-Transplantation | | | |
|---|---|---|---|
| | Median OD | (Interquartile range) | (range) |
| Acute vascular rejection (n = 20): | 140 | (96-196) | (37-331) |
| Normal renal allograft (n = 39): | 94 | (49-147) | (20-631) |

EXAMPLE 3

Figure 2:
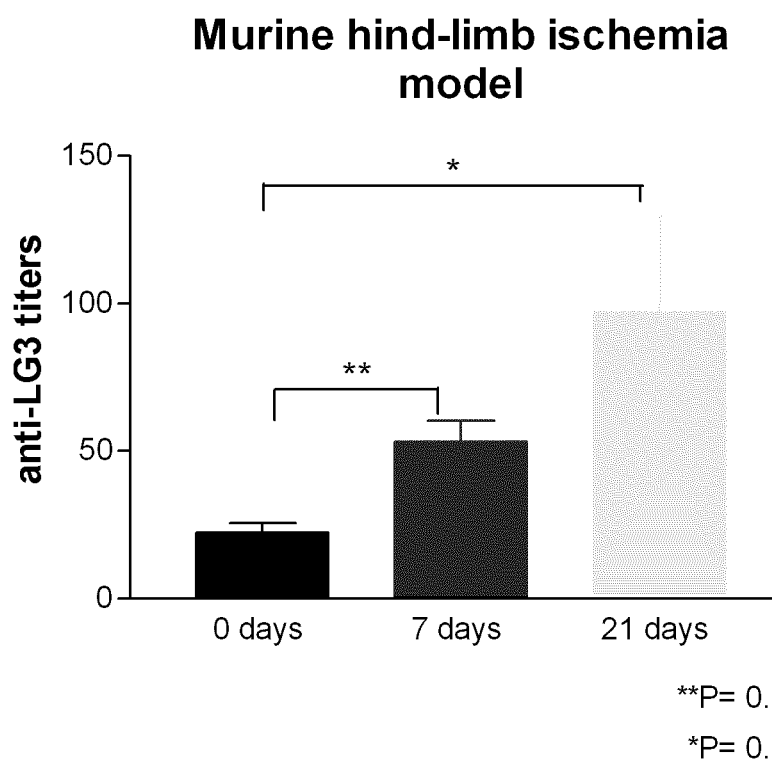
FIG. 2 shows anti-LG3 antibodies titers following hind-limb ischemia. Hind-limb ischemia was induced through femoral artery ligation. Serum was collected at baseline, 7 and 21 days following femoral artery ligation (N=6 mice per group)

Increased Levels of Anti-LG3 Antibodies Following Femoral Artery Ligation in Mice Hind-limb ischemia was induced through femoral artery ligation. Serum was collected at baseline, 7 and 21 days following femoral artery ligation. Anti-LG3 IgG titers were significantly higher one week following femoral artery ligation compared to baseline (FIG. 2). Anti-LG3 titers further increased at 21 days post-induction of hind-limb ischemia (FIG. 2). This data demonstrates that anti-LG3 levels are increased in other types of vascular damage, such as vascular damage associated with ischemia.

EXAMPLE 4

Anti-LG3 Levels as an Identifiable Risk Factor of AVR

A 41 year-old patient with end-stage renal disease secondary to diabetes mellitus type II received a de novo renal transplantation. A flow-cross match performed prior to transplantation was negative, thus demonstrating the absence anti-HLA or anti-vimentin antibodies. Function of the renal allograft was immediate with a normal renal ultrasound on post-operative day 2 and a sustained decrease in serum creatinine. On day 5 renal function deteriorated. An abdominal CT-scan and an allograft ultrasound did not demonstrate any mechanical or vascular cause for the allograft dysfunction. A renal biopsy was performed on day 7 and demonstrated acute vascular rejection (Banff IIA). C1q and C4d deposition were present in arterial compartments but negative within peritubular capillaries. A flow PRA was repeated and remained negative for all specificities, including the donor HLAs. Anti-LG3 serum levels were at 244 (OD at 450 nm) prior to transplantation and decreased abruptly to 65, co-incidentally with arterial complement activation within the allograft. This suggests that anti-LG3 antibodies were actively deposited within the allograft and contributed to complement activation and allograft dysfunction. This observation illustrates a case where the main identifiable risk factor of AVR was the presence of high titers of anti-LG3 antibodies pre-transplantation.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

---

What is claimed is:

1. A method for treating vascular damage in a human subject in need thereof, said method comprising:
   (i) identifying a human subject suffering from vascular damage by:
      (a) measuring a level of antibodies directed against LG3 (anti-LG3) in a biological sample from said subject;
      (b) comparing said level to a control level;
      (c) identifying a subject suffering from vascular damage based on said comparison, wherein a higher level of anti-LG3 in said sample relative to said control level is indicative that said subject suffers from vascular damage; and
   (ii) providing a suitable therapy against vascular damage to said subject suffering from vascular damage.

2. The method of claim 1, wherein said subject is a solid organ transplant recipient and said vascular damage is acute vascular rejection (AVR).

3. A method for treating acute vascular rejection (AVR) in a candidate human solid organ transplant recipient at risk thereof, said method comprising:
   (i) identifying a candidate human solid organ transplant recipient at risk of suffering from AVR by:
      (a) measuring a level of antibodies directed against LG3 (anti-LG3) in a biological sample from said candidate solid organ transplant recipient;
      (b) comparing said level to a control level;
      (c) identifying a candidate solid organ transplant recipient at risk of suffering from AVR based on said comparison, wherein a higher level of anti-LG3 in said sample relative to said control level is indicative that said subject is at risk of suffering from AVR; and
   (ii) providing a suitable anti-rejection therapy to said subject at risk of suffering from AVR.

4. The method of claim 2, wherein said solid organ transplant is renal transplant.

5. The method of claim 3, wherein said level of anti-LG3 is measured by an immunoassay.

6. The method of claim 5, wherein said measuring comprises:
   (i) contacting said biological sample with an LG3 polypeptide bound to a solid support to allow the formation of anti-LG3 -LG3 polypeptide complex;
   (ii) contacting said solid support with a second antibody recognizing said anti-LG3; and
   (iii) measuring the level of said second antibody bound to said solid support.

7. The method of claim 6, wherein said second antibody is labeled or conjugated.

8. The method of claim 7, wherein said second antibody is conjugated to an enzyme.

9. The method of claim 8, wherein said enzyme is horseradish peroxidase (HRP).

10. The method of claim 3, wherein said biological sample is a serum sample.

11. An assay mixtures comprising (i) a recombinant human LG3 polypeptide; and
   (ii) a biological sample from a human solid organ transplant recipient.

12. The assay mixture of claim 11, wherein said biological sample is a serum sample.

13. The assay mixture of claim 11, wherein said LG3 polypeptide is bound to an assay plate.

14. The assay mixture of claim 11, further comprising an anti-human IgG antibody.

15. The method of claim 3, wherein said solid organ transplant is renal transplant.

16. The method of claim 1, wherein said level of anti-LG3 is measured by an immunoassay.

17. The method of claim 16, wherein said measuring comprises:
   (i) contacting said biological sample with an LG3 polypeptide bound to a solid support to allow the formation of anti-LG3 -LG3 polypeptide complex;
   (ii) contacting said solid support with a second antibody recognizing said anti-LG3; and
   (iii) measuring the level of said second antibody bound to said solid support.

18. The method of claim 17, wherein said second antibody is labeled or conjugated.

19. The method of claim 1, wherein said biological sample is a serum sample.

* * * * *

SEQUENCE LISTING

```
<160> NUMBER OF SEQ ID NOS: 1

<210> SEQ ID NO 1
<211> LENGTH: 4391
<212> TYPE: PRT
<213> ORGANISM: Homo sapiens

<400> SEQUENCE: 1

Met Gly Trp Arg Ala Ala Gly Ala Leu Leu Leu Ala Leu Leu Leu His
1               5                   10                  15

Gly Arg Leu Leu Ala Val Thr His Gly Leu Arg Ala Tyr Asp Gly Leu
            20                  25                  30

Ser Leu Pro Glu Asp Ile Glu Thr Val Thr Ala Ser Gln Met Arg Trp
        35                  40                  45

Thr His Ser Tyr Leu Ser Asp Asp Glu Asp Met Leu Ala Asp Ser Ile
    50                  55                  60

Ser Gly Asp Asp Leu Gly Ser Gly Asp Leu Gly Ser Gly Asp Phe Gln
65                  70                  75                  80

Met Val Tyr Phe Arg Ala Leu Val Asn Phe Thr Arg Ser Ile Glu Tyr
                85                  90                  95

Ser Pro Gln Leu Glu Asp Ala Gly Ser Arg Glu Phe Arg Glu Val Ser
            100                 105                 110

Glu Ala Val Val Asp Thr Leu Glu Ser Glu Tyr Leu Lys Ile Pro Gly
        115                 120                 125

Asp Gln Val Val Ser Val Val Phe Ile Lys Glu Leu Asp Gly Trp Val
    130                 135                 140

Phe Val Glu Leu Asp Val Gly Ser Glu Gly Asn Ala Asp Gly Ala Gln
145                 150                 155                 160

Ile Gln Glu Met Leu Leu Arg Val Ile Ser Ser Gly Ser Val Ala Ser
                165                 170                 175

Tyr Val Thr Ser Pro Gln Gly Phe Gln Phe Arg Arg Leu Gly Thr Val
            180                 185                 190
```

```
Pro Gln Phe Pro Arg Ala Cys Thr Glu Ala Glu Phe Ala Cys His Ser
        195                 200                 205
Tyr Asn Glu Cys Val Ala Leu Glu Tyr Arg Cys Asp Arg Arg Pro Asp
    210                 215                 220
Cys Arg Asp Met Ser Asp Glu Leu Asn Cys Glu Glu Pro Val Leu Gly
225                 230                 235                 240
Ile Ser Pro Thr Phe Ser Leu Leu Val Glu Thr Thr Ser Leu Pro Pro
                245                 250                 255
Arg Pro Glu Thr Thr Ile Met Arg Gln Pro Pro Val Thr His Ala Pro
            260                 265                 270
Gln Pro Leu Leu Pro Gly Ser Val Arg Pro Leu Pro Cys Gly Pro Gln
        275                 280                 285
Glu Ala Ala Cys Arg Asn Gly His Cys Ile Pro Arg Asp Tyr Leu Cys
    290                 295                 300
Asp Gly Gln Glu Asp Cys Glu Asp Gly Ser Asp Glu Leu Asp Cys Gly
305                 310                 315                 320
Pro Pro Pro Pro Cys Glu Pro Asn Glu Phe Pro Cys Gly Asn Gly His
                325                 330                 335
Cys Ala Leu Lys Leu Trp Arg Cys Asp Gly Asp Phe Asp Cys Glu Asp
            340                 345                 350
Arg Thr Asp Glu Ala Asn Cys Pro Thr Lys Arg Pro Glu Glu Val Cys
        355                 360                 365
Gly Pro Thr Gln Phe Arg Cys Val Ser Thr Asn Met Cys Ile Pro Ala
    370                 375                 380
Ser Phe His Cys Asp Glu Glu Ser Asp Cys Pro Asp Arg Ser Asp Glu
385                 390                 395                 400
Phe Gly Cys Met Pro Pro Gln Val Val Thr Pro Pro Arg Glu Ser Ile
                405                 410                 415
Gln Ala Ser Arg Gly Gln Thr Val Thr Phe Thr Cys Val Ala Ile Gly
            420                 425                 430
Val Pro Thr Pro Ile Ile Asn Trp Arg Leu Asn Trp Gly His Ile Pro
        435                 440                 445
Ser His Pro Arg Val Thr Val Thr Ser Glu Gly Gly Arg Gly Thr Leu
    450                 455                 460
Ile Ile Arg Asp Val Lys Glu Ser Asp Gln Gly Ala Tyr Thr Cys Glu
465                 470                 475                 480
Ala Met Asn Ala Arg Gly Met Val Phe Gly Ile Pro Asp Gly Val Leu
                485                 490                 495
Glu Leu Val Pro Gln Arg Gly Pro Cys Pro Asp Gly His Phe Tyr Leu
            500                 505                 510
Glu His Ser Ala Ala Cys Leu Pro Cys Phe Cys Phe Gly Ile Thr Ser
        515                 520                 525
Val Cys Gln Ser Thr Arg Arg Phe Arg Asp Gln Ile Arg Leu Arg Phe
    530                 535                 540
Asp Gln Pro Asp Asp Phe Lys Gly Val Asn Val Thr Met Pro Ala Gln
545                 550                 555                 560
Pro Gly Thr Pro Pro Leu Ser Ser Thr Gln Leu Gln Ile Asp Pro Ser
                565                 570                 575
Leu His Glu Phe Gln Leu Val Asp Leu Ser Arg Arg Phe Leu Val His
            580                 585                 590
Asp Ser Phe Trp Ala Leu Pro Glu Gln Phe Leu Gly Asn Lys Val Asp
        595                 600                 605
Ser Tyr Gly Gly Ser Leu Arg Tyr Asn Val Arg Tyr Glu Leu Ala Arg
```

-continued

```
            610                 615                 620
Gly Met Leu Glu Pro Val Gln Arg Pro Asp Val Val Leu Met Gly Ala
625                 630                 635                 640

Gly Tyr Arg Leu Leu Ser Arg Gly His Thr Pro Thr Gln Pro Gly Ala
                645                 650                 655

Leu Asn Gln Arg Gln Val Gln Phe Ser Glu His Trp Val His Glu
                    660                 665                 670

Ser Gly Arg Pro Val Gln Arg Ala Glu Leu Leu Gln Val Leu Gln Ser
            675                 680                 685

Leu Glu Ala Val Leu Ile Gln Thr Val Tyr Asn Thr Lys Met Ala Ser
690                 695                 700

Val Gly Leu Ser Asp Ile Ala Met Asp Thr Thr Val Thr His Ala Thr
705                 710                 715                 720

Ser His Gly Arg Ala His Ser Val Glu Glu Cys Arg Cys Pro Ile Gly
                725                 730                 735

Tyr Ser Gly Leu Ser Cys Glu Ser Cys Asp Ala His Phe Thr Arg Val
                740                 745                 750

Pro Gly Gly Pro Tyr Leu Gly Thr Cys Ser Gly Cys Asn Cys Asn Gly
            755                 760                 765

His Ala Ser Ser Cys Asp Pro Val Tyr Gly His Cys Leu Asn Cys Gln
770                 775                 780

His Asn Thr Glu Gly Pro Gln Cys Asn Lys Cys Lys Ala Gly Phe Phe
785                 790                 795                 800

Gly Asp Ala Met Lys Ala Thr Ala Thr Ser Cys Arg Pro Cys Pro Cys
                805                 810                 815

Pro Tyr Ile Asp Ala Ser Arg Arg Phe Ser Asp Thr Cys Phe Leu Asp
                820                 825                 830

Thr Asp Gly Gln Ala Thr Cys Asp Ala Cys Ala Pro Gly Tyr Thr Gly
            835                 840                 845

Arg Arg Cys Glu Ser Cys Ala Pro Gly Tyr Glu Gly Asn Pro Ile Gln
850                 855                 860

Pro Gly Gly Lys Cys Arg Pro Val Asn Gln Glu Ile Val Arg Cys Asp
865                 870                 875                 880

Glu Arg Gly Ser Met Gly Thr Ser Gly Glu Ala Cys Arg Cys Lys Asn
                885                 890                 895

Asn Val Val Gly Arg Leu Cys Asn Glu Cys Ala Asp Gly Ser Phe His
                900                 905                 910

Leu Ser Thr Arg Asn Pro Asp Gly Cys Leu Lys Cys Phe Cys Met Gly
            915                 920                 925

Val Ser Arg His Cys Thr Ser Ser Ser Trp Ser Arg Ala Gln Leu His
930                 935                 940

Gly Ala Ser Glu Glu Pro Gly His Phe Ser Leu Thr Asn Ala Ala Ser
945                 950                 955                 960

Thr His Thr Thr Asn Glu Gly Ile Phe Ser Pro Thr Pro Gly Glu Leu
                965                 970                 975

Gly Phe Ser Ser Phe His Arg Leu Leu Ser Gly Pro Tyr Phe Trp Ser
            980                 985                 990

Leu Pro Ser Arg Phe Leu Gly Asp Lys Val Thr Ser Tyr Gly Gly Glu
            995                 1000                1005

Leu Arg Phe Thr Val Thr Gln Arg Ser Gln Pro Gly Ser Thr Pro
    1010                1015                1020

Leu His Gly Gln Pro Leu Val Val Leu Gln Gly Asn Asn Ile Ile
    1025                1030                1035
```

-continued

Leu Glu His His Val Ala Gln Glu Pro Ser Pro Gly Gln Pro Ser
    1040            1045                1050

Thr Phe Ile Val Pro Phe Arg Glu Gln Ala Trp Gln Arg Pro Asp
    1055            1060                1065

Gly Gln Pro Ala Thr Arg Glu His Leu Leu Met Ala Leu Ala Gly
    1070            1075                1080

Ile Asp Thr Leu Leu Ile Arg Ala Ser Tyr Ala Gln Gln Pro Ala
    1085            1090                1095

Glu Ser Arg Val Ser Gly Ile Ser Met Asp Val Ala Val Pro Glu
    1100            1105                1110

Glu Thr Gly Gln Asp Pro Ala Leu Glu Val Glu Gln Cys Ser Cys
    1115            1120                1125

Pro Pro Gly Tyr Arg Gly Pro Ser Cys Gln Asp Cys Asp Thr Gly
    1130            1135                1140

Tyr Thr Arg Thr Pro Ser Gly Leu Tyr Leu Gly Thr Cys Glu Arg
    1145            1150                1155

Cys Ser Cys His Gly His Ser Glu Ala Cys Glu Pro Glu Thr Gly
    1160            1165                1170

Ala Cys Gln Gly Cys Gln His His Thr Glu Gly Pro Arg Cys Glu
    1175            1180                1185

Gln Cys Gln Pro Gly Tyr Tyr Gly Asp Ala Gln Arg Gly Thr Pro
    1190            1195                1200

Gln Asp Cys Gln Leu Cys Pro Cys Tyr Gly Asp Pro Ala Ala Gly
    1205            1210                1215

Gln Ala Ala His Thr Cys Phe Leu Asp Thr Asp Gly His Pro Thr
    1220            1225                1230

Cys Asp Ala Cys Ser Pro Gly His Ser Gly Arg His Cys Glu Arg
    1235            1240                1245

Cys Ala Pro Gly Tyr Tyr Gly Asn Pro Ser Gln Gly Gln Pro Cys
    1250            1255                1260

Gln Arg Asp Ser Gln Val Pro Gly Pro Ile Gly Cys Asn Cys Asp
    1265            1270                1275

Pro Gln Gly Ser Val Ser Ser Gln Cys Asp Ala Ala Gly Gln Cys
    1280            1285                1290

Gln Cys Lys Ala Gln Val Glu Gly Leu Thr Cys Ser His Cys Arg
    1295            1300                1305

Pro His His Phe His Leu Ser Ala Ser Asn Pro Asp Gly Cys Leu
    1310            1315                1320

Pro Cys Phe Cys Met Gly Ile Thr Gln Gln Cys Ala Ser Ser Ala
    1325            1330                1335

Tyr Thr Arg His Leu Ile Ser Thr His Phe Ala Pro Gly Asp Phe
    1340            1345                1350

Gln Gly Phe Ala Leu Val Asn Pro Gln Arg Asn Ser Arg Leu Thr
    1355            1360                1365

Gly Glu Phe Thr Val Glu Pro Val Pro Glu Gly Ala Gln Leu Ser
    1370            1375                1380

Phe Gly Asn Phe Ala Gln Leu Gly His Glu Ser Phe Tyr Trp Gln
    1385            1390                1395

Leu Pro Glu Thr Tyr Gln Gly Asp Lys Val Ala Ala Tyr Gly Gly
    1400            1405                1410

Lys Leu Arg Tyr Thr Leu Ser Tyr Thr Ala Gly Pro Gln Gly Ser
    1415            1420                1425

```
Pro Leu Ser Asp Pro Asp Val Gln Ile Thr Gly Asn Asn Ile Met
    1430            1435                1440

Leu Val Ala Ser Gln Pro Ala Leu Gln Gly Pro Glu Arg Arg Ser
1445            1450                1455

Tyr Glu Ile Met Phe Arg Glu Glu Phe Trp Arg Arg Pro Asp Gly
    1460            1465                1470

Gln Pro Ala Thr Arg Glu His Leu Leu Met Ala Leu Ala Asp Leu
1475            1480                1485

Asp Glu Leu Leu Ile Arg Ala Thr Phe Ser Ser Val Pro Leu Ala
    1490            1495                1500

Ala Ser Ile Ser Ala Val Ser Leu Glu Val Ala Gln Pro Gly Pro
1505            1510                1515

Ser Asn Arg Pro Arg Ala Leu Glu Val Glu Glu Cys Arg Cys Pro
    1520            1525                1530

Pro Gly Tyr Ile Gly Leu Ser Cys Gln Asp Cys Ala Pro Gly Tyr
1535            1540                1545

Thr Arg Thr Gly Ser Gly Leu Tyr Leu Gly His Cys Glu Leu Cys
    1550            1555                1560

Glu Cys Asn Gly His Ser Asp Leu Cys His Pro Glu Thr Gly Ala
1565            1570                1575

Cys Ser Gln Cys Gln His Asn Ala Ala Gly Glu Phe Cys Glu Leu
    1580            1585                1590

Cys Ala Pro Gly Tyr Tyr Gly Asp Ala Thr Ala Gly Thr Pro Glu
1595            1600                1605

Asp Cys Gln Pro Cys Ala Cys Pro Leu Thr Asn Pro Glu Asn Met
    1610            1615                1620

Phe Ser Arg Thr Cys Glu Ser Leu Gly Ala Gly Gly Tyr Arg Cys
1625            1630                1635

Thr Ala Cys Glu Pro Gly Tyr Thr Gly Gln Tyr Cys Glu Gln Cys
    1640            1645                1650

Gly Pro Gly Tyr Val Gly Asn Pro Ser Val Gln Gly Gly Gln Cys
1655            1660                1665

Leu Pro Glu Thr Asn Gln Ala Pro Leu Val Val Glu Val His Pro
    1670            1675                1680

Ala Arg Ser Ile Val Pro Gln Gly Gly Ser His Ser Leu Arg Cys
1685            1690                1695

Gln Val Ser Gly Ser Pro Pro His Tyr Phe Tyr Trp Ser Arg Glu
    1700            1705                1710

Asp Gly Arg Pro Val Pro Ser Gly Thr Gln Gln Arg His Gln Gly
1715            1720                1725

Ser Glu Leu His Phe Pro Ser Val Gln Pro Ser Asp Ala Gly Val
    1730            1735                1740

Tyr Ile Cys Thr Cys Arg Asn Leu His Gln Ser Asn Thr Ser Arg
1745            1750                1755

Ala Glu Leu Leu Val Thr Glu Ala Pro Ser Lys Pro Ile Thr Val
    1760            1765                1770

Thr Val Glu Glu Gln Arg Ser Gln Ser Val Arg Pro Gly Ala Asp
1775            1780                1785

Val Thr Phe Ile Cys Thr Ala Lys Ser Lys Ser Pro Ala Tyr Thr
    1790            1795                1800

Leu Val Trp Thr Arg Leu His Asn Gly Lys Leu Pro Thr Arg Ala
1805            1810                1815

Met Asp Phe Asn Gly Ile Leu Thr Ile Arg Asn Val Gln Leu Ser
```

```
                    1820                1825                1830

Asp Ala Gly Thr Tyr Val Cys Thr Gly Ser Asn Met Phe Ala Met
    1835                1840                1845

Asp Gln Gly Thr Ala Thr Leu His Val Gln Ala Ser Gly Thr Leu
    1850                1855                1860

Ser Ala Pro Val Val Ser Ile His Pro Pro Gln Leu Thr Val Gln
    1865                1870                1875

Pro Gly Gln Leu Ala Glu Phe Arg Cys Ser Ala Thr Gly Ser Pro
    1880                1885                1890

Thr Pro Thr Leu Glu Trp Thr Gly Gly Pro Gly Gln Leu Pro
    1895                1900                1905

Ala Lys Ala Gln Ile His Gly Gly Ile Leu Arg Leu Pro Ala Val
    1910                1915                1920

Glu Pro Thr Asp Gln Ala Gln Tyr Leu Cys Arg Ala His Ser Ser
    1925                1930                1935

Ala Gly Gln Gln Val Ala Arg Ala Val Leu His Val His Gly Gly
    1940                1945                1950

Gly Gly Pro Arg Val Gln Val Ser Pro Glu Arg Thr Gln Val His
    1955                1960                1965

Ala Gly Arg Thr Val Arg Leu Tyr Cys Arg Ala Ala Gly Val Pro
    1970                1975                1980

Ser Ala Thr Ile Thr Trp Arg Lys Glu Gly Gly Ser Leu Pro Pro
    1985                1990                1995

Gln Ala Arg Ser Glu Arg Thr Asp Ile Ala Thr Leu Leu Ile Pro
    2000                2005                2010

Ala Ile Thr Thr Ala Asp Ala Gly Phe Tyr Leu Cys Val Ala Thr
    2015                2020                2025

Ser Pro Ala Gly Thr Ala Gln Ala Arg Ile Gln Val Val Val Leu
    2030                2035                2040

Ser Ala Ser Asp Ala Ser Pro Pro Pro Val Lys Ile Glu Ser Ser
    2045                2050                2055

Ser Pro Ser Val Thr Glu Gly Gln Thr Leu Asp Leu Asn Cys Val
    2060                2065                2070

Val Ala Gly Ser Ala His Ala Gln Val Thr Trp Tyr Arg Arg Gly
    2075                2080                2085

Gly Ser Leu Pro Pro His Thr Gln Val His Gly Ser Arg Leu Arg
    2090                2095                2100

Leu Pro Gln Val Ser Pro Ala Asp Ser Gly Glu Tyr Val Cys Arg
    2105                2110                2115

Val Glu Asn Gly Ser Gly Pro Lys Glu Ala Ser Ile Thr Val Ser
    2120                2125                2130

Val Leu His Gly Thr His Ser Gly Pro Ser Tyr Thr Pro Val Pro
    2135                2140                2145

Gly Ser Thr Arg Pro Ile Arg Ile Glu Pro Ser Ser His Val
    2150                2155                2160

Ala Glu Gly Gln Thr Leu Asp Leu Asn Cys Val Val Pro Gly Gln
    2165                2170                2175

Ala His Ala Gln Val Thr Trp His Lys Arg Gly Gly Ser Leu Pro
    2180                2185                2190

Ala Arg His Gln Thr His Gly Ser Leu Leu Arg Leu His Gln Val
    2195                2200                2205

Thr Pro Ala Asp Ser Gly Glu Tyr Val Cys His Val Val Gly Thr
    2210                2215                2220
```

-continued

Ser Gly Pro Leu Glu Ala Ser Val Leu Val Thr Ile Glu Ala Ser
2225                2230                2235

Val Ile Pro Gly Pro Ile Pro Pro Val Arg Ile Glu Ser Ser Ser
2240                2245                2250

Ser Thr Val Ala Glu Gly Gln Thr Leu Asp Leu Ser Cys Val Val
2255                2260                2265

Ala Gly Gln Ala His Ala Gln Val Thr Trp Tyr Lys Arg Gly Gly
2270                2275                2280

Ser Leu Pro Ala Arg His Gln Val Arg Gly Ser Arg Leu Tyr Ile
2285                2290                2295

Phe Gln Ala Ser Pro Ala Asp Ala Gly Gln Tyr Val Cys Arg Ala
2300                2305                2310

Ser Asn Gly Met Glu Ala Ser Ile Thr Val Thr Val Thr Gly Thr
2315                2320                2325

Gln Gly Ala Asn Leu Ala Tyr Pro Ala Gly Ser Thr Gln Pro Ile
2330                2335                2340

Arg Ile Glu Pro Ser Ser Ser Gln Val Ala Glu Gly Gln Thr Leu
2345                2350                2355

Asp Leu Asn Cys Val Val Pro Gly Gln Ser His Ala Gln Val Thr
2360                2365                2370

Trp His Lys Arg Gly Gly Ser Leu Pro Val Arg His Gln Thr His
2375                2380                2385

Gly Ser Leu Leu Arg Leu Tyr Gln Ala Ser Pro Ala Asp Ser Gly
2390                2395                2400

Glu Tyr Val Cys Arg Val Leu Gly Ser Ser Val Pro Leu Glu Ala
2405                2410                2415

Ser Val Leu Val Thr Ile Glu Pro Ala Gly Ser Val Pro Ala Leu
2420                2425                2430

Gly Val Thr Pro Thr Val Arg Ile Glu Ser Ser Ser Ser Gln Val
2435                2440                2445

Ala Glu Gly Gln Thr Leu Asp Leu Asn Cys Leu Val Ala Gly Gln
2450                2455                2460

Ala His Ala Gln Val Thr Trp His Lys Arg Gly Gly Ser Leu Pro
2465                2470                2475

Ala Arg His Gln Val His Gly Ser Arg Leu Arg Leu Leu Gln Val
2480                2485                2490

Thr Pro Ala Asp Ser Gly Glu Tyr Val Cys Arg Val Val Gly Ser
2495                2500                2505

Ser Gly Thr Gln Glu Ala Ser Val Leu Val Thr Ile Gln Gln Arg
2510                2515                2520

Leu Ser Gly Ser His Ser Gln Gly Val Ala Tyr Pro Val Arg Ile
2525                2530                2535

Glu Ser Ser Ser Ala Ser Leu Ala Asn Gly His Thr Leu Asp Leu
2540                2545                2550

Asn Cys Leu Val Ala Ser Gln Ala Pro His Thr Ile Thr Trp Tyr
2555                2560                2565

Lys Arg Gly Gly Ser Leu Pro Ser Arg His Gln Ile Val Gly Ser
2570                2575                2580

Arg Leu Arg Ile Pro Gln Val Thr Pro Ala Asp Ser Gly Glu Tyr
2585                2590                2595

Val Cys His Val Ser Asn Gly Ala Gly Ser Arg Glu Thr Ser Leu
2600                2605                2610

```
Ile Val Thr Ile Gln Gly Ser Gly Ser Ser His Val Pro Ser Val
2615                2620                2625

Ser Pro Pro Ile Arg Ile Glu Ser Ser Pro Thr Val Val Glu
2630                2635                2640

Gly Gln Thr Leu Asp Leu Asn Cys Val Val Ala Arg Gln Pro Gln
2645                2650                2655

Ala Ile Ile Thr Trp Tyr Lys Arg Gly Gly Ser Leu Pro Ser Arg
2660                2665                2670

His Gln Thr His Gly Ser His Leu Arg Leu His Gln Met Ser Val
2675                2680                2685

Ala Asp Ser Gly Glu Tyr Val Cys Arg Ala Asn Asn Ile Asp
2690                2695                2700

Ala Leu Glu Ala Ser Ile Val Ile Ser Val Ser Pro Ser Ala Gly
2705                2710                2715

Ser Pro Ser Ala Pro Gly Ser Ser Met Pro Ile Arg Ile Glu Ser
2720                2725                2730

Ser Ser Ser His Val Ala Glu Gly Glu Thr Leu Asp Leu Asn Cys
2735                2740                2745

Val Val Pro Gly Gln Ala His Ala Gln Val Thr Trp His Lys Arg
2750                2755                2760

Gly Gly Ser Leu Pro Ser His His Gln Thr Arg Gly Ser Arg Leu
2765                2770                2775

Arg Leu His His Val Ser Pro Ala Asp Ser Gly Glu Tyr Val Cys
2780                2785                2790

Arg Val Met Gly Ser Ser Gly Pro Leu Glu Ala Ser Val Leu Val
2795                2800                2805

Thr Ile Glu Ala Ser Gly Ser Ser Ala Val His Val Pro Ala Pro
2810                2815                2820

Gly Gly Ala Pro Pro Ile Arg Ile Glu Pro Ser Ser Ser Arg Val
2825                2830                2835

Ala Glu Gly Gln Thr Leu Asp Leu Lys Cys Val Val Pro Gly Gln
2840                2845                2850

Ala His Ala Gln Val Thr Trp His Lys Arg Gly Gly Asn Leu Pro
2855                2860                2865

Ala Arg His Gln Val His Gly Pro Leu Leu Arg Leu Asn Gln Val
2870                2875                2880

Ser Pro Ala Asp Ser Gly Glu Tyr Ser Cys Gln Val Thr Gly Ser
2885                2890                2895

Ser Gly Thr Leu Glu Ala Ser Val Leu Val Thr Ile Glu Pro Ser
2900                2905                2910

Ser Pro Gly Pro Ile Pro Ala Pro Gly Leu Ala Gln Pro Ile Tyr
2915                2920                2925

Ile Glu Ala Ser Ser Ser His Val Thr Glu Gly Gln Thr Leu Asp
2930                2935                2940

Leu Asn Cys Val Val Pro Gly Gln Ala His Ala Gln Val Thr Trp
2945                2950                2955

Tyr Lys Arg Gly Gly Ser Leu Pro Ala Arg His Gln Thr His Gly
2960                2965                2970

Ser Gln Leu Arg Leu His Leu Val Ser Pro Ala Asp Ser Gly Glu
2975                2980                2985

Tyr Val Cys Arg Ala Ala Ser Gly Pro Gly Pro Glu Gln Glu Ala
2990                2995                3000

Ser Phe Thr Val Thr Val Pro Pro Ser Glu Gly Ser Ser Tyr Arg
```

-continued

```
             3005                3010                3015
Leu Arg Ser Pro Val Ile Ser Ile Asp Pro Pro Ser Ser Thr Val
        3020                3025                3030
Gln Gln Gly Gln Asp Ala Ser Phe Lys Cys Leu Ile His Asp Gly
        3035                3040                3045
Ala Ala Pro Ile Ser Leu Glu Trp Lys Thr Arg Asn Gln Glu Leu
        3050                3055                3060
Glu Asp Asn Val His Ile Ser Pro Asn Gly Ser Ile Ile Thr Ile
        3065                3070                3075
Val Gly Thr Arg Pro Ser Asn His Gly Thr Tyr Arg Cys Val Ala
        3080                3085                3090
Ser Asn Ala Tyr Gly Val Ala Gln Ser Val Val Asn Leu Ser Val
        3095                3100                3105
His Gly Pro Pro Thr Val Ser Val Leu Pro Glu Gly Pro Val Trp
        3110                3115                3120
Val Lys Val Gly Lys Ala Val Thr Leu Glu Cys Val Ser Ala Gly
        3125                3130                3135
Glu Pro Arg Ser Ser Ala Arg Trp Thr Arg Ile Ser Ser Thr Pro
        3140                3145                3150
Ala Lys Leu Glu Gln Arg Thr Tyr Gly Leu Met Asp Ser His Ala
        3155                3160                3165
Val Leu Gln Ile Ser Ser Ala Lys Pro Ser Asp Ala Gly Thr Tyr
        3170                3175                3180
Val Cys Leu Ala Gln Asn Ala Leu Gly Thr Ala Gln Lys Gln Val
        3185                3190                3195
Glu Val Ile Val Asp Thr Gly Ala Met Ala Pro Gly Ala Pro Gln
        3200                3205                3210
Val Gln Ala Glu Glu Ala Glu Leu Thr Val Glu Ala Gly His Thr
        3215                3220                3225
Ala Thr Leu Arg Cys Ser Ala Thr Gly Ser Pro Ala Pro Thr Ile
        3230                3235                3240
His Trp Ser Lys Leu Arg Ser Pro Leu Pro Trp Gln His Arg Leu
        3245                3250                3255
Glu Gly Asp Thr Leu Ile Ile Pro Arg Val Ala Gln Gln Asp Ser
        3260                3265                3270
Gly Gln Tyr Ile Cys Asn Ala Thr Ser Pro Ala Gly His Ala Glu
        3275                3280                3285
Ala Thr Ile Ile Leu His Val Glu Ser Pro Pro Tyr Ala Thr Thr
        3290                3295                3300
Val Pro Glu His Ala Ser Val Gln Ala Gly Glu Thr Val Gln Leu
        3305                3310                3315
Gln Cys Leu Ala His Gly Thr Pro Pro Leu Thr Phe Gln Trp Ser
        3320                3325                3330
Arg Val Gly Ser Ser Leu Pro Gly Arg Ala Thr Ala Arg Asn Glu
        3335                3340                3345
Leu Leu His Phe Glu Arg Ala Ala Pro Glu Asp Ser Gly Arg Tyr
        3350                3355                3360
Arg Cys Arg Val Thr Asn Lys Val Gly Ser Ala Glu Ala Phe Ala
        3365                3370                3375
Gln Leu Leu Val Gln Gly Pro Pro Gly Ser Leu Pro Ala Thr Ser
        3380                3385                3390
Ile Pro Ala Gly Ser Thr Pro Thr Val Gln Val Thr Pro Gln Leu
        3395                3400                3405
```

```
Glu Thr Lys Ser Ile Gly Ala Ser Val Glu Phe His Cys Ala Val
    3410            3415                3420

Pro Ser Asp Arg Gly Thr Gln Leu Arg Trp Phe Lys Glu Gly Gly
    3425            3430                3435

Gln Leu Pro Pro Gly His Ser Val Gln Asp Gly Val Leu Arg Ile
    3440            3445                3450

Gln Asn Leu Asp Gln Ser Cys Gln Gly Thr Tyr Ile Cys Gln Ala
    3455            3460                3465

His Gly Pro Trp Gly Lys Ala Gln Ala Ser Ala Gln Leu Val Ile
    3470            3475                3480

Gln Ala Leu Pro Ser Val Leu Ile Asn Ile Arg Thr Ser Val Gln
    3485            3490                3495

Thr Val Val Val Gly His Ala Val Glu Phe Glu Cys Leu Ala Leu
    3500            3505                3510

Gly Asp Pro Lys Pro Gln Val Thr Trp Ser Lys Val Gly Gly His
    3515            3520                3525

Leu Arg Pro Gly Ile Val Gln Ser Gly Val Val Arg Ile Ala
    3530            3535                3540

His Val Glu Leu Ala Asp Ala Gly Gln Tyr Arg Cys Thr Ala Thr
    3545            3550                3555

Asn Ala Ala Gly Thr Thr Gln Ser His Val Leu Leu Leu Val Gln
    3560            3565                3570

Ala Leu Pro Gln Ile Ser Met Pro Gln Glu Val Arg Val Pro Ala
    3575            3580                3585

Gly Ser Ala Ala Val Phe Pro Cys Ile Ala Ser Gly Tyr Pro Thr
    3590            3595                3600

Pro Asp Ile Ser Trp Ser Lys Leu Asp Gly Ser Leu Pro Pro Asp
    3605            3610                3615

Ser Arg Leu Glu Asn Asn Met Leu Met Leu Pro Ser Val Arg Pro
    3620            3625                3630

Gln Asp Ala Gly Thr Tyr Val Cys Thr Ala Thr Asn Arg Gln Gly
    3635            3640                3645

Lys Val Lys Ala Phe Ala His Leu Gln Val Pro Glu Arg Val Val
    3650            3655                3660

Pro Tyr Phe Thr Gln Thr Pro Tyr Ser Phe Leu Pro Leu Pro Thr
    3665            3670                3675

Ile Lys Asp Ala Tyr Arg Lys Phe Glu Ile Lys Ile Thr Phe Arg
    3680            3685                3690

Pro Asp Ser Ala Asp Gly Met Leu Leu Tyr Asn Gly Gln Lys Arg
    3695            3700                3705

Val Pro Gly Ser Pro Thr Asn Leu Ala Asn Arg Gln Pro Asp Phe
    3710            3715                3720

Ile Ser Phe Gly Leu Val Gly Gly Arg Pro Glu Phe Arg Phe Asp
    3725            3730                3735

Ala Gly Ser Gly Met Ala Thr Ile Arg His Pro Thr Pro Leu Ala
    3740            3745                3750

Leu Gly His Phe His Thr Val Thr Leu Leu Arg Ser Leu Thr Gln
    3755            3760                3765

Gly Ser Leu Ile Val Gly Asp Leu Ala Pro Val Asn Gly Thr Ser
    3770            3775                3780

Gln Gly Lys Phe Gln Gly Leu Asp Leu Asn Glu Glu Leu Tyr Leu
    3785            3790                3795
```

-continued

```
Gly Gly Tyr Pro Asp Tyr Gly Ala Ile Pro Lys Ala Gly Leu Ser
        3800            3805            3810

Ser Gly Phe Ile Gly Cys Val Arg Glu Leu Arg Ile Gln Gly Glu
3815            3820            3825

Glu Ile Val Phe His Asp Leu Asn Leu Thr Ala His Gly Ile Ser
        3830            3835            3840

His Cys Pro Thr Cys Arg Asp Arg Pro Cys Gln Asn Gly Gly Gln
3845            3850            3855

Cys His Asp Ser Glu Ser Ser Tyr Val Cys Val Cys Pro Ala
        3860            3865            3870

Gly Phe Thr Gly Ser Arg Cys Glu His Ser Gln Ala Leu His Cys
3875            3880            3885

His Pro Glu Ala Cys Gly Pro Asp Ala Thr Cys Val Asn Arg Pro
        3890            3895            3900

Asp Gly Arg Gly Tyr Thr Cys Arg Cys His Leu Gly Arg Ser Gly
3905            3910            3915

Leu Arg Cys Glu Glu Gly Val Thr Val Thr Thr Pro Ser Leu Ser
        3920            3925            3930

Gly Ala Gly Ser Tyr Leu Ala Leu Pro Ala Leu Thr Asn Thr His
3935            3940            3945

His Glu Leu Arg Leu Asp Val Glu Phe Lys Pro Leu Ala Pro Asp
        3950            3955            3960

Gly Val Leu Leu Phe Ser Gly Gly Lys Ser Gly Pro Val Glu Asp
3965            3970            3975

Phe Val Ser Leu Ala Met Val Gly Gly His Leu Glu Phe Arg Tyr
        3980            3985            3990

Glu Leu Gly Ser Gly Leu Ala Val Leu Arg Ser Ala Glu Pro Leu
3995            4000            4005

Ala Leu Gly Arg Trp His Arg Val Ser Ala Glu Arg Leu Asn Lys
        4010            4015            4020

Asp Gly Ser Leu Arg Val Asn Gly Gly Arg Pro Val Leu Arg Ser
4025            4030            4035

Ser Pro Gly Lys Ser Gln Gly Leu Asn Leu His Thr Leu Leu Tyr
        4040            4045            4050

Leu Gly Gly Val Glu Pro Ser Val Pro Leu Ser Pro Ala Thr Asn
4055            4060            4065

Met Ser Ala His Phe Arg Gly Cys Val Gly Glu Val Ser Val Asn
        4070            4075            4080

Gly Lys Arg Leu Asp Leu Thr Tyr Ser Phe Leu Gly Ser Gln Gly
4085            4090            4095

Ile Gly Gln Cys Tyr Asp Ser Ser Pro Cys Glu Arg Gln Pro Cys
        4100            4105            4110

Gln His Gly Ala Thr Cys Met Pro Ala Gly Glu Tyr Glu Phe Gln
4115            4120            4125

Cys Leu Cys Arg Asp Gly Phe Lys Gly Asp Leu Cys Glu His Glu
        4130            4135            4140

Glu Asn Pro Cys Gln Leu Arg Glu Pro Cys Leu His Gly Gly Thr
4145            4150            4155

Cys Gln Gly Thr Arg Cys Leu Cys Leu Pro Gly Phe Ser Gly Pro
        4160            4165            4170

Arg Cys Gln Gln Gly Ser Gly His Gly Ile Ala Glu Ser Asp Trp
4175            4180            4185

His Leu Glu Gly Ser Gly Gly Asn Asp Ala Pro Gly Gln Tyr Gly
```

-continued

```
              4190            4195              4200
Ala Tyr Phe His Asp Asp Gly Phe Leu Ala Phe Pro Gly His Val
    4205            4210              4215
Phe Ser Arg Ser Leu Pro Glu Val Pro Glu Thr Ile Glu Leu Glu
    4220            4225              4230
Val Arg Thr Ser Thr Ala Ser Gly Leu Leu Leu Trp Gln Gly Val
    4235            4240              4245
Glu Val Gly Glu Ala Gly Gln Gly Lys Asp Phe Ile Ser Leu Gly
    4250            4255              4260
Leu Gln Asp Gly His Leu Val Phe Arg Tyr Gln Leu Gly Ser Gly
    4265            4270              4275
Glu Ala Arg Leu Val Ser Glu Asp Pro Ile Asn Asp Gly Glu Trp
    4280            4285              4290
His Arg Val Thr Ala Leu Arg Glu Gly Arg Arg Gly Ser Ile Gln
    4295            4300              4305
Val Asp Gly Glu Glu Leu Val Ser Gly Arg Ser Pro Gly Pro Asn
    4310            4315              4320
Val Ala Val Asn Ala Lys Gly Ser Val Tyr Ile Gly Gly Ala Pro
    4325            4330              4335
Asp Val Ala Thr Leu Thr Gly Gly Arg Phe Ser Ser Gly Ile Thr
    4340            4345              4350
Gly Cys Val Lys Asn Leu Val Leu His Ser Ala Arg Pro Gly Ala
    4355            4360              4365
Pro Pro Pro Gln Pro Leu Asp Leu Gln His Arg Ala Gln Ala Gly
    4370            4375              4380
Ala Asn Thr Arg Pro Cys Pro Ser
    4385            4390
```